Nov. 28, 1950 E. S. BOERNER Plant Pat. 992
ROSE PLANT
Filed Jan. 26, 1950
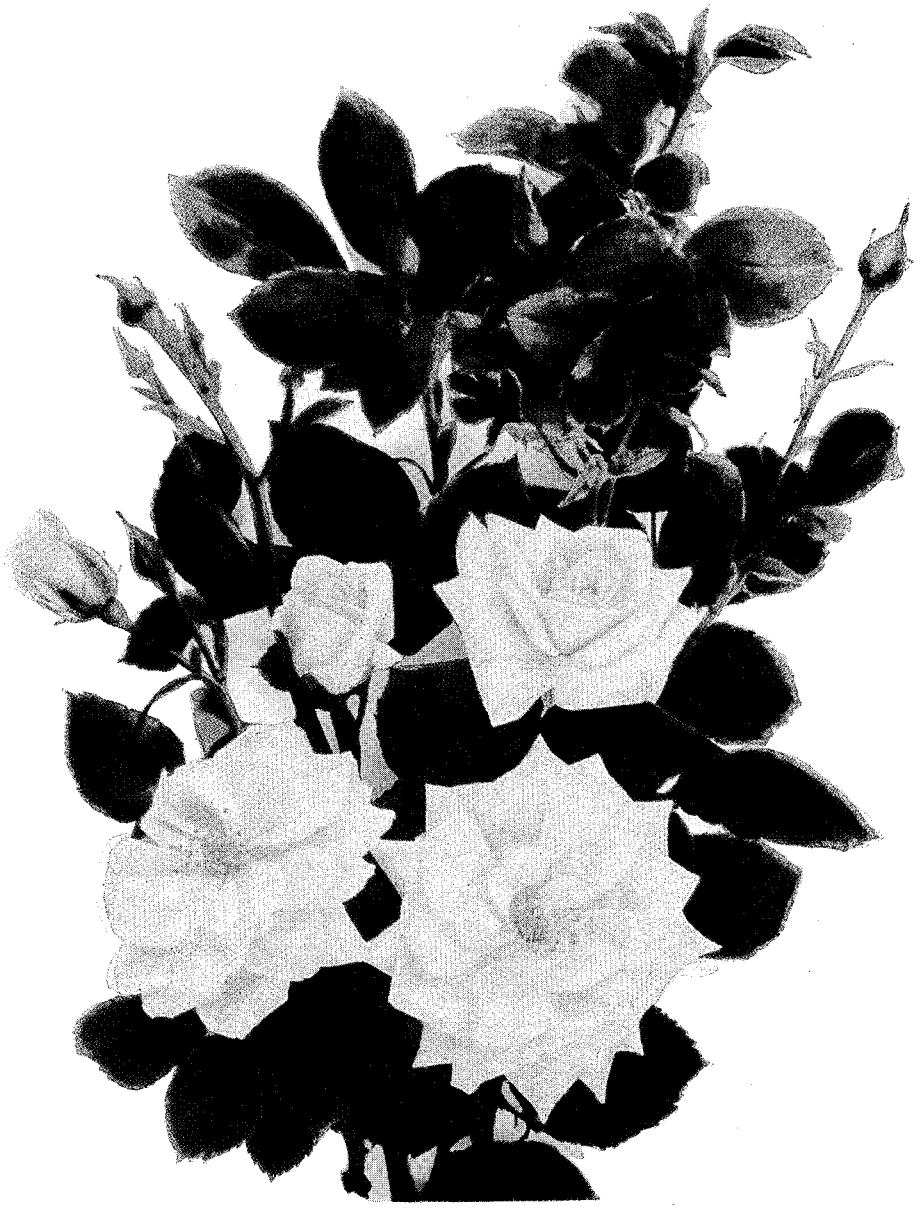
Inventor.
E. S. Boerner
By: Robert Cobb
Attorneys Patented Nov. 28, 1950

Plant Pat. 992

UNITED STATES PATENT OFFICE

992

ROSE PLANT

Eugene S. Boerner, Newark, N. Y., assignor to Jackson & Perkins Company, Newark, N. Y., a corporation of New York Application January 26, 1950, Serial No. 140,627

1 Claim. (Cl. 47—61)

The present invention relates to a new and distinct variety of rose plant of the large-flowered polyantha class, originated by crossing the yellow floribunda variety "Goldilocks" (Plant Patent No. 672) with the white to cream mutation "Marionette" (Plant Patent No. 569).

The primary objective sought in making this cross was to obtain a true yellow color of the blooms, combined with the general plant and foliage characteristics of the floribunda variety "Pinocchio" (Plant Patent No. 484). The particular seedling resulting from this cross achieved this objective in a marked and striking way, with the still further improvements in the perfect form of the individual blooms and the steady floriferousness of the new variety.

Asexual reproduction of the new variety by budding at Newark, New York, Pleasanton, California, and elsewhere, where the observations were made for the disclosure herein, shows that these characteristics come true to form and are established and fixed through succeeding propagations.

The accompanying drawing shows a group of the flowers and foliage of this new variety, with the flowers at different stages of development from small bud to full open bloom, as observed in the gardens in early August, 1949, at about 11:00 a. m.

The following is a detailed description of the new variety, color terminology being in accordance with Ridgway's Color Standards and Nomenclature:

Parentage: Seedling.
*Seed parent.*—"Goldilocks."
*Pollen parent.*—"Marionette."
Classification: Botanic—large-flowered polyantha. Commercial—floribunda.

*Flower*

Blooming habit: Recurrent—continuous.
Bud:
*Size.*—Medium.
*Form.*—Pointed; ovoid. Is not affected by wet or hot weather.
*Color.*—When sepals first divide—Carmine, Plate 1. When petals begin to unfurl—Apricot Yellow, Plate 4. When half blown—inside of petals—Empire Yellow, Plate 4. Reverse of petals—Empire Yellow, Plate 4.
*Sepals.*—Branched. Curl back when petals begin to unfurl. Color—inside—Light Viridine Green, Plate 6; outside—Light Bice Green, Plate 17.

*Calyx.*—Shape—funnel. Size—small. Aspect—smooth. Color—Parrot Green, Plate 6.
*Peduncle.*—Length—medium. Aspect—rough. Color—Medal Bronze, Plate 4. Strength—erect; slender.
*Opening.*—Opens up well. Is not affected by adverse weather conditions.
Bloom:
*Size.*—Large. Average size when fully expanded, 2½"–3".
*Borne.*—In clusters; rounded.
*Stems.*—Medium length; strong.
*Form.*—When first open—cupped. Permanence—outer petals curl back.
*Petalage.*—Double (full but open center). Number of petals under normal conditions, 35–40.
*Color.*—Center of flower—Empire Yellow, Plate 4. Outer petals—Martius Yellow, Plate 4, overcast with Naphthalene Yellow, Plate 16. Base of petals (aiglet)—Pale Lemon Yellow, Plate 4. Inside of petals—Pinard Yellow, Plate 4. Reverse of petals—Naphthalene Yellow, Plate 16. General tonality from a distance—Empire Yellow, Plate 4.
*Discoloration.*—General tonality at end of first day—Empire Yellow, Plate 4. Second day—Pinard Yellow, Plate 4. Third day—Martius Yellow, Plate 4, overcast with Naphthalene Yellow, Plate 16.
Petals:
*Texture.*—Thin. Is not affected by wet or hot weather.
*Appearance.*—Inside—shiny; outside—satiny.
*Form.*—Oval.
*Arrangement.*—Irregular. Petaloids in center—few; small.
*Persistence.*—Drop off cleanly.
*Fragrance.*—Slight. Nature—tea (average hybrid tea scent).
*Lasting quality.*—On the plant and as cut flower—long.
Genital organs:
*Stamens, anthers.*—Medium size; few. Color—Apricot Yellow, Plate 4. Arrangement—regular around styles.
*Stamens, filaments.*—Medium length. Color—Citron Yellow, Plate 16.
*Pollen.*—Color—Baryta Yellow, Plate 4.
*Styles.*—Columnar, uneven length; medium length; thin.
*Stigmas.*—Color—Martius Yellow, Plate 4.
*Ovaries.*—All enclosed in calyx.

3

*Plant*

Form: Bush.
Growth: Vigorous; compact.
Foliage: 3–5 leaflets.
*Size.*—Medium.
*Quantity.*—Abundant.
*Color.*—New foliage: upper side—Grass Green, Plate 6, overcast with Victoria Lake, Plate 1. Serrations—Victoria Lake, Plate 1; under side—Yellowish Oil Green, Plate 5, lightly overcast with Victoria Lake, Plate 1. Old foliage: upper side—Cress Green, Plate 31; under side—Rainette Green, Plate 31.
*Shape.*—Oval pointed.
*Texture.*—Upper side—leathery; under side—smooth. Ribs and veins—ordinary.
*Edge.*—Serrated (saw toothed).
*Serration.*—Double; small.
*Leaf stem.*—Color—Citron Green, Plate 31. Under side—prickles.
*Stipules.*—Medium length; bearded.
*Disease resistance.*—Resistant.

4

Wood:
*New wood.*—Color—Hay's Russet, Plate 14. Bark—smooth.
*Old wood.*—Color—Light Cress Green, Plate 31. Bark—smooth.
Thorns:
*Thorns.*—Quantity—on main stalks from base and on laterals from stalk—many. Form — narrow base; medium length; straight. Color when young—Acajou Red, Plate 13. Position—irregular.
*Prickles.*—None.
*Hairs.*—None.

I claim:

A new and distinct variety of rose plant, characterized as to novelty by the true yellow color and perfect form of the individual large-flowered polyantha type blooms, combined with the general plant and foliage characteristics of the floribunda variety "Pinocchio" (Plant Patent No. 484), and the steady floriferousness of the variety, substantially as shown and described.

EUGENE S. BOERNER.

No references cited.